(12) United States Patent
Okuyama

(10) Patent No.: US 12,029,629 B2
(45) Date of Patent: Jul. 9, 2024

(54) ADHESIVE PATCH FOR BODY SURFACE

(71) Applicant: ALCARE CO., LTD., Tokyo (JP)

(72) Inventor: Wataru Okuyama, Tokyo (JP)

(73) Assignee: ALCARE CO., LTD., Tokyo (JP)

( * ) Notice: Subject to any disclaimer, the term of this patent is extended or adjusted under 35 U.S.C. 154(b) by 135 days.

(21) Appl. No.: 17/256,323

(22) PCT Filed: Jun. 27, 2019

(86) PCT No.: PCT/JP2019/025514
§ 371 (c)(1),
(2) Date: Dec. 28, 2020

(87) PCT Pub. No.: WO2020/004519
PCT Pub. Date: Jan. 2, 2020

(65) Prior Publication Data
US 2021/0259891 A1   Aug. 26, 2021

(30) Foreign Application Priority Data

Jun. 28, 2018 (JP) ................................. 2018-122743

(51) Int. Cl.
*A61F 13/0246* (2024.01)
*A61F 13/02* (2024.01)

(52) U.S. Cl.
CPC ...... *A61F 13/0253* (2013.01); *A61F 13/0259* (2013.01)

(58) Field of Classification Search
CPC .... A61G 13/0253; A61N 5/1029; A61N 5/10; A61N 5/1001; A61N 5/1028; A61L 15/58; A61L 15/00; A61L 15/16; A61L 15/42; A61L 26/00; A61L 24/00; A61K 9/7061; A61F 13/0253; A61F 2013/0296; A61F 13/00; A61F 13/02; A61F 13/0259;
(Continued)

(56) References Cited

U.S. PATENT DOCUMENTS 4,595,001 A * 6/1986 Potter ..................... A61L 15/26
128/846
10,556,038 B2 * 2/2020 Watanabe ............... A61L 15/58
(Continued)

FOREIGN PATENT DOCUMENTS

CN      104812865 A      7/2015
CN    201980043178.5    9/2021
(Continued)

OTHER PUBLICATIONS

Kawamoto et al., "Double-sided adhesive tape", Mar. 14, 2018, All pages (Year: 2018).*
(Continued)

*Primary Examiner* — Caitlin A Carreiro
*Assistant Examiner* — Haley Virginia Frye
(74) *Attorney, Agent, or Firm* — WC&F IP

(57) ABSTRACT

A body surface patch is provided that includes: a substrate having a top face and a bottom face; an adhesive layer covering at least part of the bottom face of the substrate; and a releasable adhesive protecting film covering the adhesive layer. The substrate has a thickness of 20 to 90 μm and the adhesive layer has a thickness of 40 to 160 μm. The adhesive layer at least contains a radiation curable resin and a hydrophilic polymer compound.

5 Claims, 1 Drawing Sheet

(58) Field of Classification Search
CPC ........ A61F 13/0293; A61F 2013/00089; A61F 2013/00289; A61F 2013/00336; A61F 2013/00361; A61F 2013/00387; A61F 2013/0068; A61F 2013/15894; A61F 2013/00582; Y10T 428/28; B05D 3/061
USPC .... 602/41–43, 52, 54, 57, 58; 604/304, 307; 424/448; 523/111; 427/487, 558
See application file for complete search history.

(56) References Cited

U.S. PATENT DOCUMENTS

| | | | |
|---|---|---|---|
| 2002/0164446 A1* | 11/2002 | Zhou | A61L 15/58 428/40.1 |
| 2007/0077282 A1* | 4/2007 | Shirai | A61K 31/60 424/448 |
| 2007/0243353 A1* | 10/2007 | Kubo | A61F 13/0243 428/40.1 |
| 2013/0017246 A1* | 1/2013 | Tunius | A61F 13/0206 522/66 |
| 2013/0165875 A1* | 6/2013 | Choi | A61P 25/00 604/307 |
| 2016/0121018 A1 | 5/2016 | Watanabe et al. | |
| 2016/0346422 A1* | 12/2016 | Watanabe | A61F 13/0253 |
| 2018/0243463 A1 | 8/2018 | Chatterjee et al. | |

FOREIGN PATENT DOCUMENTS

| | | | | |
|---|---|---|---|---|
| EP | 2924092 | | 9/2015 | |
| JP | H09-154872 A | | 6/1997 | |
| JP | 2010-018564 A | | 1/2010 | |
| JP | 2014-176646 A | | 9/2014 | |
| JP | 6294541 B1 | * | 3/2018 | ............. B32B 27/00 |
| WO | 2014080954 A1 | | 5/2014 | |
| WO | 2015119160 A1 | | 8/2015 | |
| WO | WO-2016167931 A1 | * | 10/2016 | ............. A61F 13/15 |

OTHER PUBLICATIONS

European Patent Office search report dated Mar. 3, 2022.
English language translation of International Search Report of PCT/JP2019/025514, dated Sep. 17, 2019.
Office Action for the Japanese Application No. 2018-122743, dated Apr. 25, 2022.
Japanese Office Action dated Sep. 20, 2022.
EPO office action dated Mar. 17, 2020.
EPO office action dated Sep. 26, 2023.

* cited by examiner

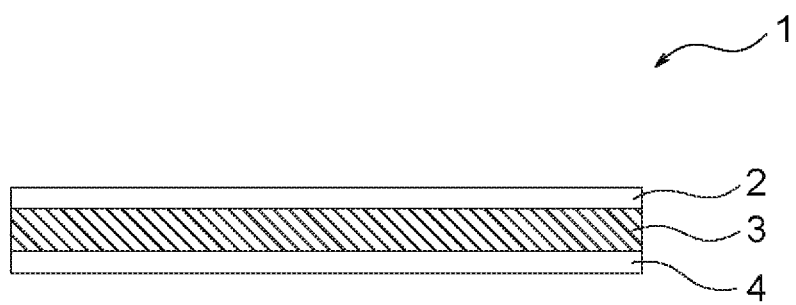

ADHESIVE PATCH FOR BODY SURFACE

TECHNICAL FIELD

The present technique relates to a body surface patch. More specifically, the present technique relates to a body surface patch that is applicable to skin or any other part on a body and usable in, for example, protection or treatment of the skin or a wound.

BACKGROUND ART

Various types of patches have been used conventionally for protection and treatment of skin, wounds, and fixation of medical supplies and medical instruments, for example, gauzes, bandages, and catheters to body surfaces.

A typical body surface patch includes a substrate and an adhesive layer on one face of the substrate and is applied to a body surface. Since such a patch is required to fit well to the profile and expansion of the body surface, thin flexible sheeted films are preferred as substrates. Unfortunately, such films used in the substrates are not generally stiff and readily bend or ruck during application of the patches to the body surfaces, resulting in poor handling ability of the patches during application of the patches.

Patent Literature 1 discloses a patch that is provided with a tentative carrier sheet stiffer than a substrate on the non-adhesive face of the substrate. After the substrate is applied on a body surface, the carrier sheet is removed.

CITATION LIST

Patent Literature

Patent Literature 1: Japanese Unexamined Patent Application Publication No. H9-154872

SUMMARY OF INVENTION

Technical Problem

Unfortunately, the carrier sheet provided on the patch complicates the structure of the patch, resulting in cumbersome application work. As a thick material or a stiff material is adapted to a substrate or an adhesive layer to keep stiffness of the patch suitably, fitness to the body surface may be reduced after application of the patch and the patch may be easily separate and remove from the body surface.

If a large amount of plasticizer is added to the adhesive to keep high flexibility and elasticity of the patch so as to fit to the profile and expansion of the body surface, the cohesion of the adhesive layer is reduced. The adhesive layer protrudes from the periphery or edges of the patch (herein after referred to as "adhesive flow") by adhering for a prolonged time. The adhesive flow may causes a disfigured body surface, such as dust adhesion to the adhesive layer or remaining adhesive after removal of the patch.

It is an object of the present technique to provide a body surface patch that has a simple structure, high handling ability during being applied, and high flexibility and elasticity that enable fitness to the profile and expansion of the body surface after being applied, and can reduce the adhesive flow.

Solution to Problem

The present inventor, who had conducted extensive study, has found that a substrate and an adhesive layer each having a thickness within a predetermined range and use of a radiation curable resin and a hydrophilic polymer compound in the adhesive layer can solve the problem, and thus have completed the technique.

The present technique provides a body surface patch that includes: a substrate having a top face and a bottom face; an adhesive layer covering at least part of the bottom face of the substrate; and a releasable adhesive protecting film covering the adhesive layer. The substrate has a thickness of 20 to 90 µm and the adhesive layer has a thickness of 40 to 160 µm. The adhesive layer contains at least, a radiation curable resin and a hydrophilic polymer compound.

Advantageous Effects of Invention

Despite a simple structure without a carrier sheet, the body surface patch according to the present technique has high handling ability during being applied, and high flexibility and elasticity that enable the patch to fit well to the profile and expansion of the body surface after being applied, and can reduce the adhesive flow.

BRIEF DESCRIPTION OF DRAWING

FIG. 1 is a cross-sectional view of a body surface patch according to an exemplary embodiment of the present technique.

DESCRIPTION OF EMBODIMENTS

A preferred embodiment that implements the present technique will now be described with reference to the accompanying drawing. It should be noted that the embodiment that will be described below is a representative one according to the present technique. Thus, the scope of the technique should not be narrowly construed. The present technique may be combined with any one of Examples or a modification thereof described below.

As illustrated in FIG. 1, a body surface patch 1 according to the present technique includes a substrate 2 having a top face and a bottom face, an adhesive layer 3 covering at least part of the bottom face of the substrate 2, and a releasable adhesive protecting film 4 covering the adhesive layer 3. The components of the body surface patch 1 will now be described in detail.

<Substrate>

As illustrated in FIG. 1, the substrate 2 has a top face and a bottom face. The top face is disposed outermost after the body surface patch 1 according to the present technique is applied to a body surface.

The substrate according to the present technique has a thickness of preferably 20 to 90 µm, more preferably 30 to 50 µm in the case of use on an unstable site, for example, a fingertip that vigorously moves. The substrate having a thickness within such a range can achieve high handling ability of the patch 1 during application of the patch 1 and high flexibility and elasticity that enables the patch 1 to fit to the profile and expansion of the body surface after application of the patch 1.

The substrate according to the present technique may be composed of a film, foam, or fabric (a non-woven, woven, or knitted fabric). Among them, the film is preferred from the viewpoints of, for example, flexibility, elasticity, appropriate moisture permeability, bacterial barrier properties, ready wiping of dirt. Examples of materials of the film include polyurethanes; polyesters, such as poly(ethylene terephthalate) and poly(butylene terephthalate); polyamides, such as nylon 6 and nylon 66; polyolefins, such as polyethylene and polypropylene; olefinic copolymers, such as ethylene-vinyl acetate copolymers (EVA), ethylene-ethyl acrylate copolymers (EEA), ethylene-methyl acrylate copolymers (EMA), ethylene-methyl methacrylate copolymers (EMMA), ethylene-methacrylic acid polymers (EMAA), ethylene-acrylic acid copolymers (EAA); poly(vinyl alcohol); poly(vinyl chloride) and poly(vinylidene chloride); and silicones, such as polydimethylsiloxane. Among them, polyethylene is preferred because it has appropriate stiffness and can be produced at a low cost. These materials may be used alone or in combination in the form of blend.

The substrate according to the present technique may be composed of a single material. Alternatively, the substrate may be a composite composed of two or more materials. The substrate may be in the form of a laminate produced by layering the same or different substrate materials.

<Adhesive Layer>

As illustrated in FIG. 1, the adhesive layer 3 covers at least part of the bottom face of the substrate 2.

The adhesive layer according to the present technique has a thickness of preferably 40 to 160 μm, more preferably 80 to 100 μm in the case of use on an unstable site, for example, a fingertip that vigorously moves. The adhesive layer having a thickness within such a range can achieve high handling ability of the patch 1 during application of the patch 1 and high flexibility and elasticity that enables the patch 1 to fit to the profile and expansion of the body surface after application of the patch 1.

The adhesive layer according to the present technique is composed of an adhesive composition containing at least a radiation curable resin and a hydrophilic polymer compound. The adhesive composition according to the present technique is liquid before being exposed to radiation to cure the radiation curable resin contained in the adhesive composition.

Throughout the specification, the adhesive composition after being exposed to radiation is referred to as "cured adhesive" to be distinguished from the adhesive composition before being exposed to the radiation.

Although the adhesive composition according to the present technique may contain the radiation curable resin and the hydrophilic polymer compound in any form, the adhesive composition is preferably in the form of hydrocolloid in which hydrophilic polymer compound is dispersed in the radiation curable resin. The hydrocolloidal adhesive composition can absorb, for example, sweat and exudate from a wound to mitigate the irritation and itching sensation of the skin due to a sweaty environment. Thus, the body surface patch according to the present technique can be appropriately used as a wound dressing. The components of the adhesive composition will now be described in detail.

(1) Radiation Curable Resin

The term "radiation curable resin" according to the present technique refers to a resin composition that is cured or cross-linked by exposure to radiation and contains at least one component of a polymer, oligomer, and monomer. For example, the radiation curable resin may be composed of a polymer prepared by polymerization of monomer molecules in the presence of a polymerization initiator, or an oligomer or monomer that can be cured or cross-linked by exposure to radiation.

The term "radiation" refers to any beam to which the adhesive composition can be exposed and given an energy that causes a curing or cross-linking reaction due to radical, cationic, or anionic polymerization. Examples of such radiation include electron beams, UV rays, infrared rays, laser beams, visible rays, ionized radiation (for example, X-rays, α-rays, β-rays, and γ-rays), microwaves, and radiofrequency waves.

The radiation curable resin according to the present technique is preferably cured or cross-linked by at least one selected from the group consisting of electron beams, visible rays, and UV rays. In other words, the radiation curable resin is preferably at least one of an electron beam curable resin, a visible ray curable resin, and an UV ray curable resin. Among them, the UV ray curable resin is preferably used. Although the radiation curable resin may have any curing reaction mechanism, radical polymerization, cationic polymerization, or photodimerization is preferred. The radical polymerization or photodimerization is more preferred.

Examples of the radiation curable resin include (meth)acrylate resins, silicone resins, urethane resins, silicone-acrylate resins, urethane-acrylate resins, and epoxy-acrylate resins. Such radiation curable resins may be used alone, in combination, or in the form of blend. The radiation curable resin according to the present technique is preferably at least one selected from the group consisting of (meth)acrylate resins, silicone-(meth)acrylate resins, urethane-(meth)acrylate resins, and epoxy-(meth)acrylate resins, among the aforementioned resins. Preferred radiation curable resins are UV ray curable (meth)acrylate resins.

Throughout the specification, the term "(meth)acrylate" refers to both "acrylate" and "methacrylate".

Preferred examples of the radiation curable resin include polymers and/or copolymers having structural units (repeating units) derived from (meth)acrylate having preferably $C_{1-20}$, more preferably $C_{2-10}$, further preferably $C_{4-8}$ alkyl groups or $C_{4-8}$ cycloalkyl groups. The alkyl groups or the cycloalkyl groups may have substituents. Examples of the substituents includes halogen, hydroxy, aryl, alkoxy, phenoxy, epoxy, norbornyl, and adamantyl. More preferred examples of the radiation curable resins having such structural units includes polymers and/or copolymers having structural units derived from butyl (meth)acrylate and/or 2-ethylhexyl (meth)acrylate. Further preferred are polymers and/or copolymers having structural units derived from butyl acrylate and/or 2-ethylhexyl acrylate. The polymers and/or copolymers having such structural units may be oligomers, which have lower molecular weights than the polymers, as will be described below.

The radiation curable resin has a mass average molecular weight $M_w$ of preferably 1000 to 250000, more preferably 1000 to 200000. The radiation curable resin having a mass average molecular weight $M_w$ within such a range can produce an adhesive composition with a low viscosity. After exposure to radiation, the mass average molecular weight increases as a result of the curing reaction, resulting in a cured adhesive having high cohesion. The mass average molecular weight $M_w$ is measured by gel permeation chromatography (GPC) using polystyrene standard samples.

The radiation curable resin according to the present technique may be a commercially available product. Examples of the commercially available radiation curable resin include "3000 series" and "3100 series" available from ThreeBond Co., Ltd., "UNIDIC" series and "TYFORCE" series available from DIC Corporation, "Yupimer" series available from Mitsubishi Chemical Corporation, "Hitaloid" series available from Hitachi Chemical Company, Ltd, "Beam Set" series available from Arakawa Chemical Industries, Ltd., "acResin" series available from BASF SE, and "UVA-2000 series" available from Toagosei Co., Ltd.

In addition to or in place of the polymer and/or copolymer having structural units derived from the aforementioned (meth)acrylate, the radiation curable resin may contain one or more polymerizable oligomers and/or monomers. The polymerizable oligomers and/or monomers can be polymerized preferably by radical or cationic polymerization, more preferably by radical polymerization.

Examples of the radically polymerizable oligomers include (meth)acrylate oligomers, polyester-acrylate oligomers, urethane-(meth)acrylate oligomers, silicone-(meth) acrylate oligomers, and epoxy-(meth)acrylate oligomers.

Examples of the radically polymerizable monomers include monomers having (meth)acryloyl groups. The monomer may have any number of (meth)acryloyl groups. Examples of such monomers include monofunctional (meth) acrylates each having one (meth)acryloyl group, difunctional (meth)acrylates each having two (meth)acryloyl groups, and multifunctional (meth)acrylates each having three or more (meth)acryloyl groups.

Examples of the cationically polymerizable oligomers and monomers include oligomers and monomers having epoxy rings, oxetane rings, oxolane rings, dioxolan rings, and vinyl ether structures, and oligomers and monomers having functional groups with such structures. Examples of the cationically polymerizable oligomers and monomers include limonene oxide compounds available from Tomoe Engineering Co., Ltd., glycidyl ether compounds available from Kyoeisha Chemical Co., Ltd. under the product name "EPOLIGHT" series, and an oxetane compound available from Toagosei Co., Ltd. under the product name "ARON OXETANE". The radiation curable resin according to the present technique preferably contains at least one selected from the group consisting of the (meth)acrylate oligomers, the urethane (meth)acrylate oligomers, and the silicone (meth)acrylate oligomer, among the aforementioned polymerizable oligomers.

The oligomer may have any molecular weight. For example, oligomers having a number average molecular weight Mn of less than 10000 (for example, 1000 to less than 10000) may be used. Oligomers having a number average molecular weight of less than 10000 are preferred because they does not cause an excess increase in the viscosity of the adhesive composition and thus facilitates processing, for example coating. Alternatively, polymerizable oligomers may be used that has a number average molecular weight Mn of 10000 or more. The number average molecular weight Mn is measured by gel permeation chromatography (GPC) using polystyrene standard samples.

The radiation curable resin may contain, for example, a polymerization initiator, an additive, and a solvent. Any polymerization initiator may be used that is known in the field of radiation curable resins. Examples of such a polymerization initiator include acetophenone initiators, benzophenone compounds, α-keto ester compounds, and benzoin compounds.

It is preferred the polymerization initiator be preliminarily bonded with chains of, for example, a polymer or an oligomer, which is a constituent of the radiation curable resin. The radiation curable resin bonded to a polymerization initiator does not require addition of a polymerization initiator and can produce a highly safe adhesive composition. Examples of such a radiation curable resin bonded to a polymerization initiator include "UV-H" series available from KOBE SPECIALITY MATERIALS (KSM) and "acResin" series available from BASF SE. Another polymerization initiator may be added to the radiation curable resin pre-bonded to a polymerization initiator. Alternatively, the prebonded polymerization initiator may be replaced with another polymerization initiator.

Examples of the photodimerizable oligomer and polymer includes oligomers and polymers having maleimide groups. Examples of such photodimerizable oligomers and polymers are maleimide-terminated polyester resins and maleimide-terminated polyether resins available from Toagosei Co., Ltd. under the product names of "UVA-2000" series.

The radiation curable resin used in the present technique may be used in any content, preferably 40 to 90 mass %, more preferably 50 to 80 mass %, based on the total mass of the adhesive composition. The radiation curable resin in a content within such a range allows the cured adhesive to have high cohesion after exposure of the adhesive composition to radiation and can produce a stable hydrocolloidal radiation curable resin containing the hydrophilic polymer compound dispersed therein.

(2) Hydrophilic Polymer Compound

The hydrophilic polymer compound according to the present technique may be any natural, semisynthetic, or synthetic hydrophilic polymer compound. The term "semisynthesis" is also referred to as partial chemical synthesis, which uses compounds isolated from natural resources, for example, plant materials, microorganisms, or cell cultures, as starting materials.

Specific examples of the natural hydrophilic polymer compounds include plant polymers, such as Arabian gum, tragacanth gum, galactan, guar gum, Locust bean gum, Karaya gum, carrageenan, pectin, agar, and starch, for example, the starch of rice, corn, potato, or wheat; microorganic polymers, such as xanthan gum, dextrin, dextran, succinoglycan, mannan, locust bean gum, and pullulan; and animal-based polymers, such as casein, albumin, and gelatin.

Specific examples of the semisynthetic hydrophilic polymer compounds include starch polymers, for example, carboxymethyl starches and methyl hydroxypropyl starches; cellulose polymers, for example, methyl cellulose, ethyl cellulose, methyl hydroxypropyl cellulose, hydroxyethyl cellulose, cellulose sodium sulfates, hydroxypropyl cellulose, carboxymethyl cellulose, sodium carboxymethyl cellulose; and alginic acid polymers, for example, sodium alginates, calcium alginate, and propylene glycol alginates).

Specific examples of the synthetic hydrophilic polymer compound include vinyl polymers, for example, poly(vinyl alcohol), polyvinyl methyl ethers, polyvinylpyrrolidone, and carboxyvinyl polymers; acryl polymers, for example, poly (sodium acrylate) and polyacrylamide; and polyethyleneimines.

In the present technique, these hydrophilic polymer compounds may be used alone or in combination. Among the hydrophilic polymer compounds preferred are at least one selected from the group consisting of sodium carboxymethyl cellulose, pectin, Karaya gums, mannans, locust bean gums, and gelatin. It is more preferred to use at least one selected from the group consisting of sodium carboxymethyl cellulose, pectin, and gelatin. The adhesive composition containing these hydrophilic polymer compounds can readily produce so-called hydrocolloid. Thus, the adhesive layer can absorb, for example, sweat and exudate from a wound to mitigate the irritation and itching sensation of the skin due to a sweaty environment.

The content of the hydrophilic polymer compound used in the present technique is preferably 5 to 35 mass %, more preferably 10 to 30 mass %, based on the total mass of the adhesive composition. A content within such a range of the hydrophilic polymer compound can significantly absorb moisture, for example, sweat and exudate. The skin irritation due to, for example, skin maceration can be mitigated. Thus, the body surface patch according to the present technique can be applied for a prolonged time.

(3) Other Components

The adhesive composition according to the present technique may further contain, for example, a tackifier, a filler, a pH adjuster, a medicinal ingredient, and a softener or plasticizer as required, within the scope that can achieve the object of the present technique.

The adhesive composition according to the present technique may contain a functional group-free acrylic polymer. The functional group-free acrylic polymer can be used to effectively reduce the viscosity of the adhesive composition, and increase the flexibility and the adhesive strength of the cured adhesive.

The term "acryl polymer" in functional group-free acrylic polymer refers to a polyacrylate or polymethacrylate, in other words, a polymer or a copolymer having a majority (50 mol % or more) of structure units derived from the acrylate and/or methacrylate. The acryl polymer preferably has 60 to 100 mol %, more preferably 70 to 100 mol %, further preferably 80 to 100 mol % structural units derived from the acrylate and/or methacrylate. The content (mol %) of the structural units, which derived from the acrylate and/or methacrylate, in the acryl polymer can be measured by nuclear magnetic resonance (NMR).

The term "non-reactive" in the functional group-free acrylic polymer indicates that the acryl polymer substantially has no functional groups other than acryloyl groups. Examples of the other functional groups include OH, COOH, epoxy groups, and alkoxysilyl groups.

The functional group-free acrylic polymer has a mass average molecular weight ($M_w$) of preferably 1000 to 9000, more preferably 1500 to 8000, further preferably 2000 to 6000 because the viscosity of the adhesive composition can be effectively reduced and the cured adhesive having high cohesion can be produced. The mass average molecular weight $M_w$ is measured by gel permeation chromatography (GPC) using polystyrene standard samples.

In order to effectively reduce the viscosity of the adhesive composition, the functional group-free acrylic polymer according to the present technique is preferably liquid at room temperature (20 to 30° C.). The solid content in the functional group-free acrylic polymer, which is liquid at room temperature, is preferably 90% or more, more preferably 95% or more, further preferably 98% or more.

The viscosity at 25° C. of the functional group-free acrylic polymer is preferably 300 to 10000 mPa·s, more preferably 400 to 6000 mPa·s, further preferably 500 to 5000 mPa·s. In the specification, the viscosity (steady flow viscosity) of the functional group-free acrylic polymer at 25° C. is measured with a single-cylinder rotational viscometer in accordance with JIS Z8803

In order to effectively reduce the viscosity of the adhesive composition, the functional group-free acrylic polymer has a glass transition point T g of preferably −100 to −20° C., more preferably −90 to −40° C., further preferably −80 to −60° C. The glass transition point $T_g$ is measured with a differential scanning calorimeter (DSC).

The functional group-free acrylic polymer in the present technique may be in any content, preferably 5 to 25 mass %, more preferably 10 to 20 mass %, based on the total mass of the adhesive composition. A content within such a range of the functional group-free acrylic polymer can effectively reduce the viscosity of the adhesive composition and effectively increase the cohesion of the cured adhesive.

The adhesive composition according to the present technique can have a dynamic viscosity of preferably 500 Pas or less, more preferably 300 Pas or less, further preferably 250 Pas or less, measured at 115° C. and 1 Hz by a technique in Examples, which will be described below, before exposure to radiation. A viscosity of the adhesive composition within such a range facilitates processing, for example, coating of the adhesive composition with a hotmelt machine.

As detailed above, the radiation curable resin in the adhesive composition according to the present technique can be cured by exposure to radiation, resulting in a cured adhesive with high cohesion. In order to produce a cured adhesive that can be readily coated and has high cohesion, the adhesive composition preferably contains 40 to 90 mass % radiation curable resin, 5 to 35 mass % hydrophilic polymer, and 5 to 25 mass % functional group-free acrylic polymer. The preferred components detailed in the specification within more preferred ranges of contents produces a more desirable adhesive composition. In detail, the adhesive layer is preferably composed of an adhesive composition containing 50 to 80 mass % UV ray curable (meth)acrylate resin as the radiation curable resin, 10 to 30 mass % at least one hydrophilic polymer compound selected from the group consisting of sodium carboxymethyl cellulose, pectin, and gelatin, and 10 to 20 mass % functional group-free acrylic polymer that is liquid at room temperature (20 to 30° C.).

(4) Production of Cured Adhesive

The cured adhesive according to the present technique is produced by exposure of the adhesive composition to radiation, in other words, the cured adhesive is the adhesive composition after exposure to the radiation.

The adhesive composition according to the present technique may be a liquid or a solid that keeps, for example, the original shape of a film or sheet. The adhesive layer according to the present technique may contain any liquid or solid adhesive composition.

In the step of exposing the adhesive composition to radiation, any dose of radiation that can cause a curing reaction of the radiation curable resin may be used. In the case that, for example, an UV ray curable resin having a thickness of 100 μm is used as the radiation curable resin, the cumulative dose of the emitted UV rays at a wavelength of 250 to 260 nm can be appropriately adjusted in a range of 10 to 1000 mJ/cm$^2$, preferably in a range of 100 to 600 mJ/cm$^2$. In the case that an electron beam curable resin is used as the radiation curable resin, the cumulative dose of emitted electron beams can be appropriately adjusted in a range of, for example, 1 to 100 kGy.

The production of the cured adhesive according to the present technique preferably involves a step of mixing the components of the adhesive composition before the exposing step. Any mixing process, for example, using an agitator, a kneader, and a roller may be employed. The time and temperature in the mixing step may be appropriately determined depending on the components contained in the adhesive composition according to the present technique.

The production of the cured adhesive according to the present technique preferably involves a step of filling a mold with the adhesive composition or dropping or applying the adhesive composition to a substrate (hereinafter, this step is generically referred to as "coating step") before the exposing step, such that the exposure to radiation causes a homogeneous curing reaction. Any known process may be employed in the coating step. For example, a common technique, such as comma coating, die coating, bar coating, knife coating, gravure roll coating, reverse roll coating, spin coating, spray coating, screen printing, dip coating, or dispensing, may be used. The cured adhesive according to the present technique is preferably applied in a density of 40 to 160 g/m² to the substrate from the viewpoint of the adhesive strength, the fitness to the skin, and the handling ability during being applied.

It is preferred to impart air permeability to the adhesive composition during the coating step. In detail, one approach for this purpose is to adjust the gap between the die coater head and the back roll to give a tension to the adhesive composition to randomly make air inlets. Another approach is to urge an embossing roll onto the adhesive composition to transcribe the profile of the embossing roll to the adhesive composition and make air inlets. Still another approach is to use a screen with holes preliminarily provided at appropriate intervals by screen printing to cause the adhesive composition to pass through the holes. A substrate may be disposed on the other side of the screen to transcribe the adhesive composition.

The adhesive composition according to the present technique can be applied with a hotmelt machine. In this case, the adhesive composition is applied at preferably 60 to 150° C., more preferably 70 to 140° C., further preferably 80 to 130° C. in view of the ready coating work and the heat resistance of the hydrophilic polymer compound in the adhesive composition.

<Adhesive Protecting Film>

As illustrated in FIG. 1, the adhesive protecting film 4 covers the adhesive layer 3 and is removable. The adhesive protecting film 4 can protect the adhesive layer 3 from, for example, dirt and facilitate handling of the body surface patch 1.

The adhesive protecting film according to the present technique may have any thickness. The thickness is typically ranges from 40 to 150 μm.

The adhesive protecting film according to the present technique may be composed of any material, for example, a synthetic resin film or paper, which is used in a traditional patch. Examples of such a material include polyester, polyethylene, and polypropylene films, and films and paper treated with silicone release agents, fluorine, or fluorine compounds. Such a protecting film may be, for example, embossed.

The adhesive protecting film according to the present technique may be composed of a highly UV-ray-transmissive material so as to be more promptly cured or cross-linked by exposure to UV rays. For example, a transparent polypropylene or polyethylene film can be used. Use of such a material enables exposure of two faces of the body surface patch to UV rays to promptly cure or cross-link the adhesive protecting film.

The adhesive protecting film according to the present technique may consist of a single layer as illustrated in FIG. 1. The adhesive protecting film may have one or more cutouts in the center or at the edge(s). Alternatively, two or more adhesive protecting films are disposed so as to overlap at the edges. In such a configuration, one adhesive protecting film can be removed whereas the other adhesive protecting film or films can remain. The body surface patch can be applied to the body surface without touching the adhesive face, resulting in an improved application operation.

<Body Surface Patch>

The body surface patch according to the present technique has a total thickness (the sum of the thicknesses of the substrate and the adhesive layer) of preferably 60 to 250 μm, more preferably 110 to 150 μm. If the total thickness of the body surface patch is over 300 μm, the body surface patch after being applied cannot fit to the profile and expansion of the body surface or may be caught at the edge, resulting in separation of the patch.

The body surface patch according to the present technique may be of any shape, for example, a polygon (such as triangle, tetragon, and diamond), a circle, or an ellipse, or may be a sheet in appropriate combination with such shapes or a tape or a roll continuously formed in a predetermined direction. The body surface patch may be sterically formed depending on the site for application or may have an incision or a slit.

Examples of uses of the body surface patch according to the present technique include wound dressings applied to living bodies, surgical tapes, tapes for fixation of catheters and drip tubes, patches for ostomy appliances, poultices, patches for fixation of electrocardiographic electrodes and magnetic induction therapy devices, and patches for skin care and beauty care. In particular, the body surface patch according to the present technique is suitable for a wound dressing because a hydrocolloidal adhesive is used as described above. The body surface patch according to the present technique can be used as a wound dressing to effectively absorb moisture, for example, sweat and exudate from a wound and provide a wet environment suitable for healing the wound, resulting in improved wound healing effects.

The body surface patch according to the present technique preferably has a flexural rigidity (bending resistance) of $0.63 \times 10^{-7}$ mN·cm or more. The body surface patch having the flexural rigidity (bending resistance) at or above such a value can keep the stiffness appropriate for application. In the specification, the flexural rigidity (bending resistance) is measured by a technique that will be described below in Examples.

The load to the body surface patch in stretched state (the stretched body surface patch) according to the present technique after 20% displacement is preferably 6.0 N/20 mm or less. The load of 6.0 N/20 mm or less to the body surface patch in stretched state enables the body surface patch to fit to the surface body even if the surface body moves, and can prevent the discomfort during application. In the case of use on an unstable site, for example a fingertip that vigorously moves, the load to the body surface patch is more preferably 4.0 N/20 mm or less. In the specification, the load to the body surface patch in stretched state is measured by a technique that will be described below in Examples.

The body surface patch according to the present technique has an adhesive flow rate of −10 to +10% in a dry state and an adhesive flow rate of 10% or less after water absorption. The adhesive flow rate within such a range can prevent the hydrocolloidal adhesive from swelling at the cross-section at the edge of the body surface patch during application and thus the body surface patch from turning back and separating. In the specification, the adhesive flow rate is measured by a technique that will be described below in Examples.

In the body surface patch according to the present technique, it is preferred that the peak of probe tacks is 10 gf or more and that the integral value of the probe tacks is 20 to 50 gfs. The peak at or above such a value can prevent the body surface patch from separating immediately after application. The integral value within such a range enables the body surface patch to fit to the body surface and exhibit appropriate adhesiveness. In the specification, the probe tack test is carried out by an approach that will be described below in Examples.

The body surface patch according to the present technique preferably has a water absorption rate of 50% or more after 24 hours. A water absorption rate within such a range can lead to prompt absorption of, for example, sweat and exudate without the deformation of the body surface patch due to water absorption and a residual adhesive after removal on the body surface. The body surface patch according to the present technique preferably has a water absorption per unit area of 0.005 $g/cm^2$ or more after 24 hours. A water absorption per unit area within such a value barely can keep its original shape without adhesive flow after water absorption and barely causes a residual adhesive after removal.

In addition, the body surface patch according to the present technique preferably has a visible light transmittance of 5.0% or more at a wavelength 550 nm. A visible light transmittance within such a range can lead to an improvement in the appearance of the body surface patch applied to a body surface and facilitate observation of the states of water absorption and the body surface without removal of the patch from the body surface. Thus, the time for replacement can be confirmed without removal of the applied body surface patch and the leakage of water and the wasteful replacement of the patch can be prevented.

<Production of Body Surface Patch>

The body surface patch according to the present technique can be produced through at least the steps of: dropping or applying the adhesive composition onto the substrate (a coating step); and exposing the adhesive composition to radiation to cure the adhesive composition (an exposing step). Alternatively, the body surface patch can be produced through at least the steps of: dropping or applying the adhesive composition onto the adhesive protecting film; laminating the substrate to the adhesive composition; and exposing the adhesive composition to radiation to cure the adhesive composition. Alternatively, the body surface patch can be produced through at least the steps of: dropping or applying the adhesive composition onto the adhesive protecting film; exposing the adhesive composition to radiation to cure the adhesive composition; and laminating the substrate to the cured adhesive layer. The coating step and the exposing step can be performed by the same techniques as those described in Section "Production of Cured Adhesive".

EXAMPLES

The present technique will now be described in more detail by way of the following examples. These examples are presented for mere illustrative purpose of the present technique, and thus, should not be construed to limit the scope of the present technique.

Example 1

An UV curable resin (65.0 mass %) (a polymer having structural units derived from butyl acrylate (available from BASF SE under the product name "acResin A260UV") as a radiation curable resin was heated to 120° C. The resin was mixed with 20.0 mass % of sodium carboxymethyl cellulose (hereinafter referred to as "CMC·Na" and available from Nippon Paper Industries Co., Ltd.) as a hydrophilic polymer and 15.0% of a functional group-free acrylic polymer (ARUFON® UP-1000 available from Toagosei Co., Ltd.). The mixture was stirred, and then preserved at a temperature at which the viscosity of the mixture was 150 Pas or less to yield an adhesive composition.

The prepared adhesive composition was applied to a sheet of paper (treated with a silicone release agent) at 120° C. with a die coater into a thickness of 100 μm. The adhesive composition was then exposed to UV rays at a wavelength of 250 to 260 nm in a cumulative dose (hereinafter referred to as "UV ray C (UVC) dose") of 240 $mJ/cm^2$ with an UV ray irradiator. The adhesive composition was laminated to a polyethylene (PE) film with a thickness of 40 μm as a substrate, to yield a body surface patch of Example 1.

Examples 2 to 5

The body surface patches according to Examples 2 to 5 were produced as in Example 1 except that the amounts of applied adhesives and the UVC doses were varied as shown in Table 1.

Example 6

The body surface patch according to Example 6 was produced as in Example 1 except that the contents of the UV ray curable resin, the CMC·Na, and the functional group-free acrylic polymer in the adhesive composition were varied to 80.0 mass %, 10.0 mass %, and 10.0 mass %, respectively, and that the thickness of the substrate was varied to that shown in Table 1.

Example 7

The body surface patch according to Example 7 was produced as in Example 1 except that the contents of the components in the resin composition were the same as those in Example 6 and that the material and the thickness of the substrate were varied as shown in Table 1.

Comparative Examples 1 and 2

The body surface patches according to Comparative Examples 1 and 2 were produced as in Example 1 except that the contents of the components in the resin composition were the same as those in Example 6 and that the material and the thickness of the substrate were varied as shown in Table 1.

<Experiment 1: Measurement of Total Thickness>

The total thickness of the substrate and the adhesive layer of the body surface patch according to each of Examples and Comparative Examples was measured with a dial thickness gauge (MODEL H available from PEACOCK) having a gauge head of φ 10 mm. The thickness of the substrate was deducted from the total thickness to calculate the thickness of the adhesive layer.

<Experiment 2: Test of Bending Resistance>

The bending resistance of the body surface patch (hereinafter also referred to as "test specimen") according to each of Examples and Comparative Examples was measured by a "41.5° cantilever method" in accordance with JIS L1912. In detail, the test was carried out as follows:

The body surface patch according to each of Example and Comparative Examples was cut into about 20 mm wide to prepare two test specimens. Each test specimen was placed on a smooth platform with one end face tilting at 41.5° such that the adhesive face is upside and one short side of the test specimen aligned with the forward end of the platform. The test specimen was then moderately slid to the tilting face. When the central point of one end of the test specimen came into contact with the tilting face of the platform, the length of the protruding portion of the test specimen was measured. The lengths of the protruding portions of the two test specimens were measured to calculate the bending resistance (flexural rigidity (mN·cm)) by Expression (1). It should be noted that the bent length in Expression (1) refers to half the length (cm) of the protruding portion of the test specimen.

[Expression 1]

Flexural Rigidity (mN·cm)=[Mass of Test Specimen per Unit Area (g/m$^2$)]×[Overall Average of Bent Lengths (cm)]$^3$×10$^{-3}$ (1)

<Experiment 3: Test of Load to Body Surface Patch in Stretched State (Stretched Body Surface Patch)>

The load (N) to the body surface patch according to each of Examples and Comparative Examples after 20% displacement was measured with a tensile tester ("Autograph AGS-X" available from Shimadzu Corporation) under the conditions of a length of 20 mm of the specimen between grips and a tension rate of 300 mm/minute in accordance with JIS Z0237. This experiment focused on a fingertip, which vigorously moves compared with other portions on the body surface and requires fitness and comfortable application of the patch. Since the stretching rate of the skin was about 20% after a finger was bent at about 45°, the load after 20% displacement was employed as an index. Each test specimen had dimensions of 20 mm (W) by 100 mm (L).

<Experiment 4: Adhesive Flow Test>

A pressurizing plate (φ 18 mm) was placed on each of the body surface patches according to Examples 1 to 5.

A load of 5 g (about 2 g/cm$^2$) was applied to the plate along its thickness. The thickness of the body surface patch at 37° C. under an atmosphere with humidity of 90% after 72 hours was measured with a dial thickness gauge (MODEL H available from PEACOCK) having a gauge head of φ 10 mm. The thickness of the body surface patch was measured within 10 seconds before the creep restoration was observed after the load was removed. The body surface patch according to each of Examples and Comparative Examples was observed in a dry state and after immersion in saline (aqueous 0.9% NaCl solution) for three hours (hereinafter referred to as "after water absorption") to calculate the variation (%) in the thickness of the test specimen after the application of the load on the basis of that of the unloaded state.

<Experiment 5: Probe Tack Test>

A load of 10 g was applied for 2 seconds at 37° C. to each of the body surface patches according to Examples 1 to 5 using a tackiness tester (available from RHESCA Corporation Limited) under the conditions of a probe diameter of 5 mm, and a drop rate of 30 mm/minute to measure the tack at the probe from which the test specimen was separated at an ascent rate of 30 mm/minute.

<Experiment 6: Test of Water Absorption Rate>

Each of the body surface patches according to Examples 1 to 5 was immersed in saline (0.9% aqueous NaCl solution) such that the adhesive layer on the substrate was upside. The body patch in the saline was placed in a thermostatic chamber at a temperature of 37° C. and a humidity of 90%. After 24 hours, the weight of the test specimen was measured to determine the water absorption rate (%) and the water absorption per unit area (g/cm$^2$) by the following expression:

[Expression 2]

Water absorption rate(%)={[weight (g) of specimen after immersion]−[weight (g) of specimen before immersion]}/[weight (g) of specimen before immersion] (2)

[Expression 3]

Water absorption per unit area (g/cm$^2$)={[weight (g) of specimen after immersion]−[weight (g) of specimen before immersion]}/[area (cm$^2$) of specimen] (3)

<Experiment 7: Test of Visible Light Transmission>

The transmittance at a wavelength of 550 nm of the body surface patch according to each of Examples and Comparative Examples was measured with an UV spectrophotometer (UV-1650PC available from Shimadzu Corporation). The reason for use of the transmittance at the wavelength of 550 nm in this experiment is that human eyes have high sensitivity to the 550 nm light.

<Experiment 8: Evaluation Test of Application to Skin>

The body surface patch according to Example 3 was applied over nails to second knuckles of six subjects to evaluate the ease of application, and the discomfort, the adhesiveness, and the unnoticeableness immediately after application, on a ten-point scale. The criteria of the evaluated items are as follows:

(1) Ease of Application

The handling ability of the body surface patch according to Example 3 during application to the nails and the finger knuckles was evaluated on Score 10 (the patch is suitably stiff and readily applicable) to Score 0 (the patch is not stiff and barely applicable).

(2) Discomfort Immediately after Application

The discomfort immediately after application of the body surface patch according to Example 3 to the nails and the finger knuckles was evaluated on Score 10 (the patch sufficiently fits to the movement of the skin and gives no sense of foreign matter, resistance, or tightness) to Score 0 (the patch does not fit to the movement of the skin and gives the sense of foreign matter, resistance, or tightness).

(3) Adhesiveness Immediately after Application

The adhesiveness of the body surface patch according to Example 3 immediately after application to the nails and the finger knuckles was evaluated on Score 10 (the patch tightly adheres to the skin) to Score 0 (The patch separates from a nail or skin immediately after application).

(4) Unnoticeableness Immediately after Application

The unnoticeableness of the body surface patch according to Example 3 after application to the nails and the finger knuckles was evaluated on Score 10 (the patch is not noticeable) to Score 0 (the patch is noticeable).

Table 1 shows the manufacturing conditions and the results of Experiments 1 to 7 for the body surface patches according to Examples 1 to 7 and Comparative Examples 1 and 2. Table 2 shows the results of Experiment 8.

TABLE 1

| | | Ex. 1 | Ex. 2 | Ex. 3 | Ex. 4 | Ex. 5 | Ex. 6 | Ex. 7 | Com. Ex. 1 | Com. Ex. 2 |
|---|---|---|---|---|---|---|---|---|---|---|
| Composition | Radiation curable resin [%] | 65.0 | 65.0 | 65.0 | 65.0 | 65.0 | 80.0 | 80.0 | 80.0 | 80.0 |
| | Hydrophilic polymer compound [%] | 20.0 | 20.0 | 20.0 | 20.0 | 20.0 | 10.0 | 10.0 | 10.0 | 10.0 |

TABLE 1-continued

|  | Ex. 1 | Ex. 2 | Ex. 3 | Ex. 4 | Ex. 5 | Ex. 6 | Ex. 7 | Com. Ex. 1 | Com. Ex. 2 |
|---|---|---|---|---|---|---|---|---|---|
| Functional group-free acrylic polymer [%] | 15.0 | 15.0 | 15.0 | 15.0 | 15.0 | 10.0 | 10.0 | 10.0 | 10.0 |
| Substrate | PE | PE | PE | PE | PE | PE | Urethane | Urethane | Urethane |
| Thickness of substrate [μm] | 40 | 40 | 40 | 40 | 40 | 70 | 50 | 15 | 100 |
| UVC dose [mJ/cm$^2$] | 240 | 350 | 350 | 350 | 480 | 240 | 240 | 240 | 240 |
| Applied adhesive [g/m$^2$] | 100 | 80 | 100 | 120 | 100 | 100 | 100 | 100 | 100 |
| Total thickness (observed) [μm] | 140 | 124 | 130 | 153 | 134 | 128 | 105 | 185 | 250 |
| Thickness of adhesive layer (calculated) [μm] | 100 | 84 | 90 | 113 | 94 | 58 | 55 | 170 | 150 |
| Bending resistance [×10$^{-7}$ mN·cm] | 0.70 | 0.77 | 1.46 | 0.64 | 1.63 | 2.38 | 2.19 | 0.61 | 4.41 |
| Load [N/20 mm] | 3.6 | 3.7 | 3.6 | 3.5 | 3.3 | 6.1 | 3.3 | 1.1 | 7.1 |
| Flow (dry state) [%] | −4 | −4 | −8 | −3 | −4 | — | — | — | — |
| Flow (wet state) [%] | 8 | 3 | 8 | 9 | 3 | — | — | — | — |
| Probe tack (peak) [gf] | 67.3 | 46.0 | 65.9 | 54.3 | 13.0 | — | — | — | — |
| Probe tack (integral) [gfs] | 40.0 | 20.9 | 35.3 | 42.3 | 29.7 | — | — | — | — |
| Water absorption rate [%] | 105 | 105 | 100 | 98 | 103 | — | — | — | — |
| Water absorption per unit area [g/cm$^2$] | 0.013 | 0.013 | 0.013 | 0.015 | 0.014 | — | — | — | — |
| Visible light transmittance [%] | 5.5 | 6.2 | 5.5 | 5.2 | 5.8 | 9.7 | 10.2 | 23.1 | 8.3 |

TABLE 2

|  | Evaluation (Score) | |
|---|---|---|
|  | Nail | Knuckle Skin |
| Ease of application | 4.0 | 4.0 |
| Discomfort | 6.3 | 6.2 |
| Adhesiveness | 6.5 | 5.8 |
| Unnoticeableness | 8.5 | 8.2 |

As shown in Tables 1 and 2, the substrate and the adhesive layer of each of the body surface patches according to Examples 1 to 7 have thicknesses within ranges of 20 to 90 μm and 40 to 160 μm, respectively. Preferred results can be thereby confirmed in the tests of the flexural rigidity (bending resistance) and the load to the body surface patch in stretched state. In particular, the evaluation by the subjects has demonstrated that the body surface patch according to Example 3 has high handling ability during application and barely gives a discomfort immediately after application to nails and finger knuckles.

The body surface patches according to Examples 1 to 5 have an adhesive flow rate of −10 to +10% in a dry state and an adhesive flow rate of 10% or less after water absorption, resulting in a reduction in the adhesive flow.

In addition, the body surface patches according to Examples 1 to 5 each have a probe tack peak of 10 gf or more and an integral probe tack of 20 to 50 gfs indicating appropriate adhesiveness. The evaluation by the subjects has demonstrated that the body surface patch according to Example 3 has high adhesiveness immediately after application.

The body surface patches according to Examples 1 to 5 each have a water absorption rate of 50% or more and thus can promptly absorb, for example, sweat and exudate. It has been demonstrated that the deformation of the patch and the production of a residual adhesive can be significantly prevented. Furthermore, the body surface patches according to Examples 1 to 5 each exhibit a water absorption per unit area of 0.005 g/cm$^2$ or more and thus can keep their original shapes without flow after water absorption and significantly prevent production of a residual adhesive.

It has been demonstrated that the body surface patches according to Examples 1 to 7 each have a visible light transmittance of 5.0% or more and thus facilitate observation of water absorption and the state of the body surface and confirmation of an appropriate time for replacement without removal of the applied patch.

The evaluation by the subjects has demonstrated that the body surface patch according to Example 3 is unnoticeable after being applied.

As described above, the body surface patches according to Examples 1 to 7 each have appropriate stiffness, high handling ability, and high fitness to the body surface, and barely causes a stimulus or discomfort. Among others, the body surface patches according to Examples 1 to 5 each exhibit an appropriate flexural rigidity (bending resistance) and a low load to the body surface patch in stretched state and thus have significant handling ability during application and high fitness after application even if being applied to an unstable site, in particular, a nail or finger knuckle that has a small circumference and vigorously moves. The body surface patches according to Examples 1 to 5 each adhered well to the body surface immediately after application and did not separate from the body surface during application. Since the total thickness of the substrate and the adhesive layer was small, the body surface patch was not caught at the edge during application and the adhesive flow barely occurred.

The substrate of the body surface patch according to Comparative Example 1 was thin and thus had insufficient flexural rigidity (bending resistance) and stiffness, resulting in a low handling ability during application of the body surface patch. The substrate of the body surface patch according to Comparative Example 2 was thick. Thus, the load to the body surface patch in stretched state was too high, gave a discomfort during application, and did not fit well to the movement of the body surface.

The body surface patch according to the present technique includes a substrate having a thickness of 20 to 90 μm and an adhesive layer having a thickness of 40 to 160 μm. The adhesive layer at least contains a radiation curable resin and a hydrophilic polymer compound. Although having a simple configuration without a carrier sheet, the body surface patch can have high handling ability during application, and high flexibility and an elasticity that enable high fitness to the body surface after application, and reduce the adhesive flow.

REFERENCE SIGNS LIST

1 body surface patch
2 substrate
3 adhesive layer
4 adhesive protecting film

The invention claimed is:

1. A body surface patch comprising:
a substrate having a top face and a bottom face;
an adhesive layer covering at least part of the bottom face of the substrate, wherein the adhesive layer was exposed to UV rays having a wavelength of 250 to 260 nm in a cumulative dose of 240 to 350 mJ/cm$^2$; and
a releasable adhesive protecting film covering the adhesive layer, wherein
the substrate is polyethylene,
the substrate has a thickness of 30 to 50 μm and the adhesive layer has a thickness of 80 to 100 μm,
the body surface patch has a sum of the thicknesses of the substrate and the adhesive layer of 110 to 150 μm,
and the adhesive layer at least comprises
50 to 80 mass % of a radiation curable resin that is a UV ray curable (meth)acrylate resin;
10 to 30 mass % of a hydrophilic polymer compound that is a sodium carboxymethyl cellulose and
10 to 20 mass % of a functional group-free acrylic polymer that is a liquid functional group-free acrylic polymer at a room temperature of 20 to 30° C.,
wherein the functional group-free acrylic polymer has a mass average molecular weight ($M_w$) of 2000 to 6000,
wherein the body surface patch has a peak of probe tacks of 10 to 67.3 gf and an integral value of the probe tacks of 20 to 50 gfs,
wherein the body surface patch in a stretched state has a load of 4.0 N/20 mm or less after 20% displacement, and
wherein the body surface patch has an adhesive flow of 10% or less after water absorption.

2. The body surface patch according to claim 1, wherein the hydrophilic polymer compound further comprises at least one substance selected from a group consisting of pectin and gelatin, wherein a content of the hydrophilic polymer compound is 10 to 30 mass %.

3. The body surface patch according to claim 2, wherein the body surface patch has a visible light transmittance of 5.0% or more at a wavelength of 550 nm.

4. The body surface patch according to claim 1, wherein the body surface patch has a visible light transmittance of 5.0% or more at a wavelength of 550 nm.

5. The body surface patch according to claim 1, wherein the UV ray curable (meth)acrylate resin is a polymer having structural units derived from butyl acrylate.

* * * * *